(12) United States Patent
Kugel et al.

(10) Patent No.: US 6,290,708 B1
(45) Date of Patent: *Sep. 18, 2001

(54) HERNIA MESH PATCH WITH SEAL STIFFENER

(75) Inventors: Robert D. Kugel, Olympia, WA (US); J. Douglas Inman, Arlington; Keith D. Biggers, Southlake, both of TX (US)

(73) Assignee: Bard ASDI Inc., Murray Hill, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/250,225

(22) Filed: Feb. 11, 1999

Related U.S. Application Data

(63) Continuation-in-part of application No. 09/006,653, filed on Jan. 14, 1998, now Pat. No. 5,916,225, which is a continuation of application No. 08/755,108, filed on Nov. 22, 1996, now Pat. No. 5,769,864, which is a continuation-in-part of application No. 08/315,249, filed on Sep. 29, 1994, now Pat. No. 5,634,931.

(60) Provisional application No. 60/095,793, filed on Aug. 7, 1998.

(51) Int. Cl.[7] .................................................. A61B 17/04
(52) U.S. Cl. ............................. 606/151; 602/44; 602/58
(58) Field of Search ................................. 606/151, 213, 606/214, 215, 110, 113; 602/44, 58

(56) References Cited

U.S. PATENT DOCUMENTS 2,671,444   3/1954   Pease, Jr. .............................. 606/151
3,054,406   9/1962   Usher ................................... 606/151

(List continued on next page.)

FOREIGN PATENT DOCUMENTS 2114282   7/1994   (CA).
0 362 113   4/1990   (EP).

(List continued on next page.)

OTHER PUBLICATIONS

"Minimally Invasive, Non–Laparoscopic, Preperitoneal, Sutureless, Inguinal Hernorrhaphy" by Robert D. Kugel (not published). See Exhibit 2 of Declaration.

(List continued on next page.)

*Primary Examiner*—Gary Jackson
(74) *Attorney, Agent, or Firm*—Wolf, Greenfield & Sacks, P.C.

(57) ABSTRACT

A hernia patch has a first layer of inert synthetic mesh material selectively sized and shaped to extend across and beyond a hernia. A second layer of inert synthetic mesh material overlies the first layer to create a generally planar configuration for the patch. The first and second layers are joined together by a seam that defines a periphery of a pouch between the layers and provides stiffness to the patch for urging the patch to conform to the generally planar configuration across the hernia, which helps to prevent folding of the patch as the surgeon withdraws his or her finger. The seam may be straight, zig-zag, sinusoidal or other configurations that effectively urge the patch to conform to a planar configuration. One of the layers has a border that extends beyond the seam and that has a free outer edge. A plurality of border slits extend from the outer edge through the border substantially to the seam. An access slit is formed in one of the layers for insertion of a surgeon's finger into the pouch to facilitate insertion of the patch into the patient and to position the patch across the hernia.

11 Claims, 2 Drawing Sheets

U.S. PATENT DOCUMENTS

| | | | |
|---|---|---|---|
| 4,007,743 | 2/1977 | Blake | 606/151 |
| 4,347,847 | 9/1982 | Usher | 606/151 |
| 4,452,245 | 6/1984 | Usher | 606/151 |
| 4,561,434 | 12/1985 | Taylor . | |
| 4,633,873 | 1/1987 | Dumican et al. | 606/151 |
| 4,655,221 | 4/1987 | Devereux | 606/151 |
| 4,693,720 | 9/1987 | Scharnberg et al. | 606/151 |
| 4,710,192 | 12/1987 | Liotta et al. . | |
| 4,769,038 | 9/1988 | Bendavid . | |
| 4,796,603 | 1/1989 | Dahlke . | |
| 4,854,316 | 8/1989 | Davis . | |
| 4,865,026 | 9/1989 | Barrett . | |
| 4,955,907 | 9/1990 | Ledergerber . | |
| 5,006,106 | 4/1991 | Angelchik . | |
| 5,059,205 | 10/1991 | El-Nounou et al. . | |
| 5,116,357 | 5/1992 | Eberbach | 606/151 |
| 5,122,155 | 6/1992 | Eberbach | 606/151 |
| 5,141,515 | 8/1992 | Eberbach | 606/151 |
| 5,147,374 | 9/1992 | Fernandez | 606/151 |
| 5,147,384 | 9/1992 | La Rocca . | |
| 5,147,387 | 9/1992 | Jansen . | |
| 5,176,692 | 1/1993 | Wilk et al. . | |
| 5,192,301 | 3/1993 | Kamiya et al. . | |
| 5,195,542 | 3/1993 | Gazielly et al. . | |
| 5,201,745 | 4/1993 | Tayot et al. . | |
| 5,254,133 | 10/1993 | Seid . | |
| 5,258,000 | 11/1993 | Gianturco . | |
| 5,290,217 | 3/1994 | Campos . | |
| 5,334,217 | 8/1994 | Das . | |
| 5,350,399 | 9/1994 | Erlebacher et al. . | |
| 5,356,432 | 10/1994 | Rutkow et al. | 606/151 |
| 5,366,460 | 11/1994 | Eberbach . | |
| 5,368,602 | 11/1994 | de la Torre . | |
| 5,370,650 | 12/1994 | Tovey et al. . | |
| 5,397,331 | 3/1995 | Himpens et al. . | |
| 5,425,744 | 6/1995 | Fagan et al. . | |
| 5,433,996 | 7/1995 | Kranzler et al. . | |
| 5,451,235 | 9/1995 | Lock et al. . | |
| 5,456,720 | 10/1995 | Schultz et al. . | |
| 5,507,811 | 4/1996 | Koike et al. . | |
| 5,593,441 | 1/1997 | Lichtenstein et al. . | |
| 5,614,284 | 3/1997 | Kranzler et al. . | |
| 5,695,525 | 12/1997 | Mulhauser et al. . | |
| 5,702,416 | 12/1997 | Kieturakis et al. . | |
| 5,716,408 | 2/1998 | Eldridge et al. . | |
| 5,743,917 | 4/1998 | Saxon . | |
| 5,766,246 | 6/1998 | Mulhauser et al. | 623/11 |
| 5,769,864 | 6/1998 | Kugel . | |
| 5,824,082 | 10/1998 | Brown . | |
| 5,836,961 | 11/1998 | Kieturakis et al. . | |
| 5,879,366 | 3/1999 | Shaw et al. | 606/151 |
| 5,916,225 | 6/1999 | Kugel | 606/151 |
| 5,919,232 | 7/1999 | Chaffringeon et al. | 606/151 |
| 5,922,026 | 7/1999 | Chin . | |
| 5,954,767 | 9/1999 | Pajotin et al. . | |

FOREIGN PATENT DOCUMENTS

| | | |
|---|---|---|
| 0 474 887 | 10/1991 | (EP) . |
| 676 285 | 7/1979 | (SU) . |
| 782 814 | 11/1980 | (SU) . |
| WO 90/14796 | 12/1990 | (WO) . |
| WO 93/17635 | 9/1993 | (WO) . |
| WO 94/27535 | 12/1994 | (WO) . |
| WO 96/09795 | 4/1996 | (WO) . |
| WO 97/22310 | 6/1997 | (WO) . |

OTHER PUBLICATIONS

Gregory L. Brown, M.D. et al., "Comparison of Prosthetic Materials for Abdominal Wall Reconstruction in the Presence of Contamination and Infection", Annals of Surgery, Jun. 1985, vol. 201, pp. 705–711.

Scott D. Jenkins, M.D. et al., "A Comparison of Prosthetic Materials Used to Repair Abdominal Wall Defects", Surgery, Aug. 1983, vol. 94, No. 2, pp. 392–398.

"Prevention of Postsurgical Adhesions by Interceed (TC7)", Fertility and Sterility, Jun. 1989, vol. 51, No. 6, pp. 933–938.

Hernando Cordona, M.D., "Prosthokeratoplasty", 1983, Cornea, vol. 2, No. 3, 1983, pp. 179–183.

Alonzo P. Walker, M.D., et al., "Double–Layer Prostheses for Repair of Abdominal Wall Defects in a Rabbit Model", pp. 32–37, Journal of Surgical Research, vol. 55, No. No. 1, Jul. 1993.

HERNIA MESH PATCH WITH SEAL STIFFENER

CROSS-REFERENCE TO RELATED APPLICATION

This application claims the benefit of provisional application Ser. No. 60/095,793, filed Aug. 7, 1998, and is a continuation-in-part of application Ser. No. 09/006,653, filed Jan. 14, 1998, U.S. Pat. No. 5,916,225, which was a continuation of application Ser. No. 0,8/755,108, Nov. 22, 1996, U.S. Pat. No. 5,769,864, which is a continuation-in-part of application Ser. No. 08/315,249, Sep. 29, 1994, U.S. Pat. No. 5,634,931.

TECHNICAL FIELD

The present invention generally relates to a surgically implantable patch for use in repairing a hernia or other wound. More particularly, the present invention relates to a hernia repair patch having a seal that acts to stiffen the patch to maintain the patch in a planar configuration.

BACKGROUND OF THE INVENTION

Surgically implantable mesh patches for the repair of inguinal and other abdominal wall hernias, which are intended for permanent placement within a patient's body space, have been provided and used previously. Tension free surgical repairs of hernias have been developed using synthetic mesh materials to bridge and to patch hernia defects. These repairs resulted in both a decrease in the recurrence rate as well as a decrease in the amount of a patient's post operative discomfort. Patients undergoing these more advanced procedures were able and are able to resume their normal activities sooner.

Some of these earlier techniques are somewhat complicated. Several use a plug or a locating member to fit within the hernia defect itself. Also, many of these earlier techniques were designed specifically for use in laparoscopic repair of hernias. Moreover, many of the prior inventions required suturing to the patient's body tissue. Although these medical advances are acknowledged for their usefulness and success, there remains a need or needs for more improvements in the surgical repair of hernias.

DISCLOSURE OF THE INVENTION

A hernia mesh patch for use in the surgical repair of a patient's inguinal, or other abdominal wall hernias, is disclosed for permanent placement within a patient's body space. The hernia mesh patch has a top layer and a bottom layer of an inert, synthetic mesh, preferably polypropylene mesh. The top layer and the bottom layer are secured to each other with a seam. A slit is located in one of the layers to provide access to a pouch formed between the two layers by the seam.

The seam provides stiffness for the patch, which causes the patch to assume a flattened configuration. The seam comprises an ultrasonic seal that is arranged in an oval, ovoid, loop, or ring configuration, or a partial oval, ovoid, loop or ring having a circumference slightly greater than the circumference of the interior pocket of the patch. The seal may be of a linear, zig-zag, sinusoidal, or other suitable pattern. A border on at least one of the layers extends outward past the seam. The border preferably has slits that define tabs, which fill uneven voids in the patient's tissue.

Without the need for general anesthesia, nor expensive laparoscopic instrumentation, a surgeon makes a small incision in the patient when repairing an inguinal hernia. The incision is approximately three centimeters long, arranged obliquely, and approximately two to three centimeters above the internal ring location of the inguinal hernia.

Thereafter, the surgeon uses his or her fingers to readily fold and compact the hernia mesh patch and direct the patch through the incision and into the patient's properitoneal space. The hernia mesh patch then unfolds and expands into a planar configuration due to the resiliency of the seam. The surgeon may insert a finger if through a slit formed in one of the layers of the patch and into the pouch to manipulate the patch. The surgeon then moves the hernia mesh patch to cover the defect in the patient's abdominal cavity. Thereafter, the surgeon withdraws his or her finger and secures the incision with stitches.

Soon after surgery, the patient's body reacts to the mesh of the hernia mesh patch. In a short time, the mesh becomes stuck, thereby keeping the hernia mesh patch in place. Thereafter, the patient's scar tissue grows into the mesh over a period of time, typically between thirty and sixty days, to permanently fix the hernia mesh patch in its intended position over the repaired area where the hernia was located.

Small holes may be cut through both layers of the mesh inside the seal ring, to increase friction and to minimize the sliding or migration of the hernia mesh patch after it is positioned.

BEST MODE FOR CARRYING OUT THE INVENTION

Figure 1:
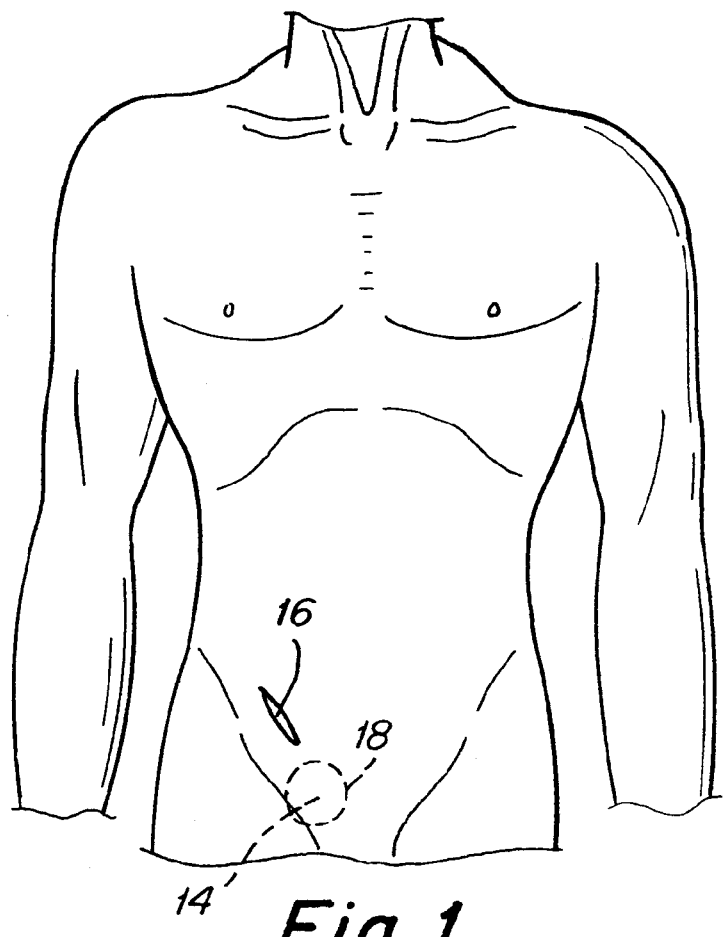
FIG. 1 is a schematic partial front view of a patient's body.
Figure 2:
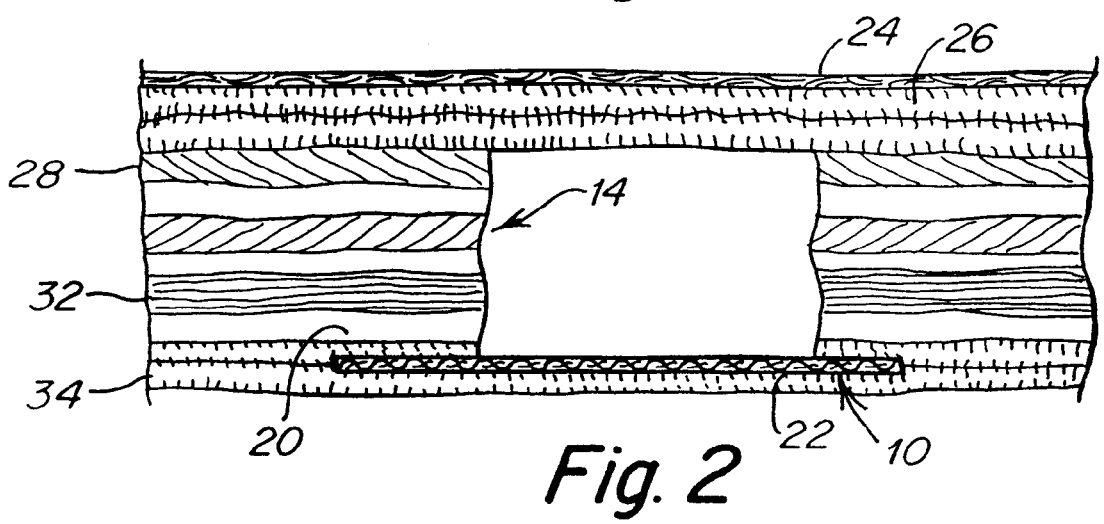
FIG. 2 is a schematic partial diagrammatic cross-section view of a patient's abdominal wall layers showing an inguinal or other abdominal wall hernia, and the surgically implantable hernia repair mesh patch positioned in the preperitoneal created space.

The hernia mesh patch 10, illustrated in the drawings, is surgically permanently implantable within a patient's body space to adequately cover, correct, prevent and repair any inguinal or other abdominal wall hernias or other types of hernias. The surgeon has the objective of making a sutureless repair by first cutting an approximately three centimeter incision 16. Incision 16 is obliquely positioned approximately two to three centimeters above the location described as the internal ring 18, where an inguinal hernia 14 has occurred, as shown in FIG. 1. The surgeon then works through incision 16 to insert the hernia mesh patch 10. The repair of an inguinal hernia is shown in FIG. 2. The surgeon dissects deeply into the patient's preperitoneal space 20, as indicated in FIG. 2, using a sharp instrument to make the incision 16 through the patient's skin 24, the subcutaneous fatty tissues 26, and the external oblique fascia 28, which has been cut parallel with its fibers a short distance. The surgeon then incises the transversalis fascia 32, creating an entrance into the preperitoneal space 20 above the peritoneum 34 at a location proximate to the hernia defect 14. In so doing, the surgeon identifies and frees up the hernia sac and creates the pocket 22 in the preperitoneal space 20. Space 20 underlies the area referred to as Hesselbach's triangle, in reference to both indirect and direct hernias. The surgeon's placement of the hernia mesh patch 10 in accordance with this method protects the entire inguinal floor, and therefore not only will the patch 10 repair or correct a single small hernia, but will also protect against future hernias through other potentially weakened areas.

Figure 3:
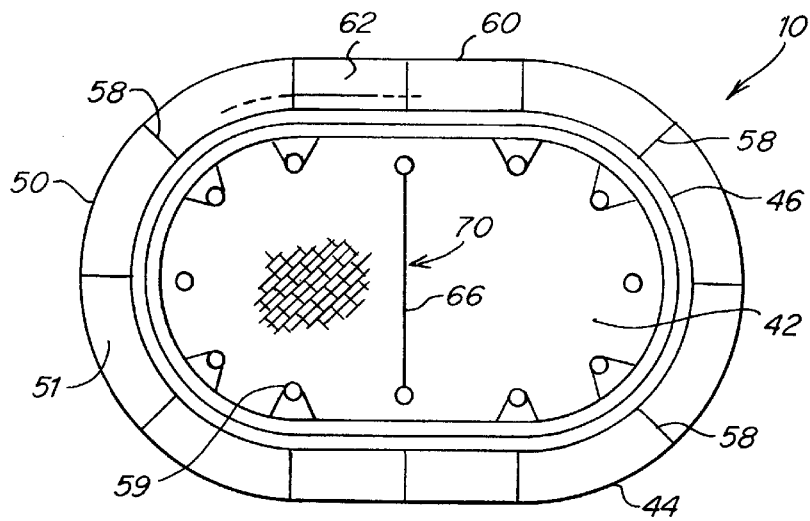
FIG. 3 is a top view of a preferred embodiment of the surgically implantable hernia repair mesh patch.

Referring now to FIGS. 2 and 3, hernia mesh patch 10 is particularly designed for the repair of an inguinal hernia 14, but also can be used for other abdominal wall hernias or other tissue aperture repair. Hernia patch 10 is composed of two similarly shaped pieces of an inert synthetic mesh material, a bottom layer 42 and a top layer 44. Bottom layer 42 and top layer 44 are preferably constructed of a polypropylene material. The mesh material is formed from monofilament material that is resistant to infection and that has been used safely in many hernia operations, in previous ways and in previous embodiments. Preferably, the layers 42, 44 are made in respective circle, loop, ovoid, or oval shapes.

Figure 7:
FIG. 7 is a top view of a zig-zag seam used in an alternate embodiment of the invention.

A seam 46 joins the top and bottom layers 44 and 42 together. Preferably, bottom layer 42 is the same size as top layer 44, although the sizes may differ slightly. Seam 46 is preferably created ultrasonically without heat, glue, etc. In one embodiment, seam 46 is located approximately one centimeter in from outer edge or periphery 50. The seam 46 may be straight (FIG. 3), zig-zag 47 (FIG. 7), sinusoidal, or in other configurations.

Figure 4:
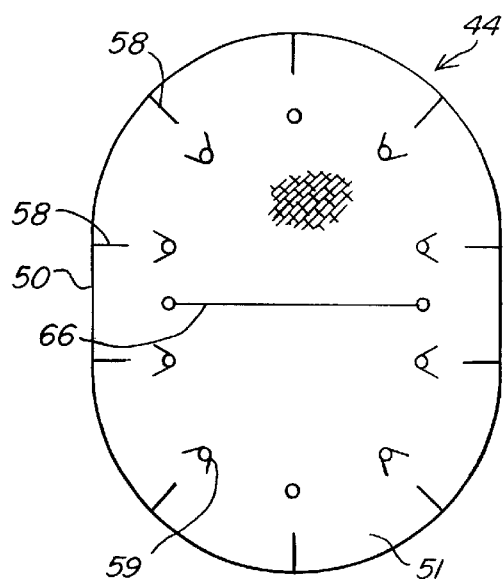
FIG. 4 is a top view of the top layer of the surgically implantable hernia repair mesh patch shown in FIG. 3.
Figure 5:
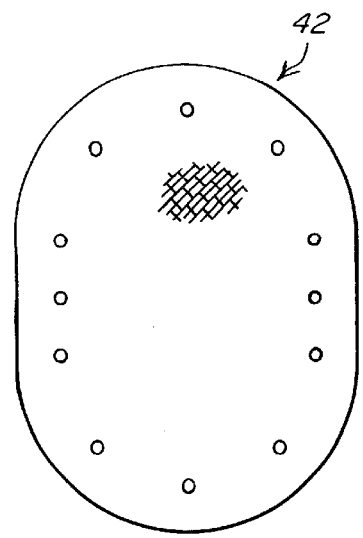
FIG. 5 is a top view of the bottom layer of the implantable hernia repair mesh patch shown in FIG. 3.
Figure 6:
FIG. 6 is an enlarged view of a dart shown in FIGS. 3 and 4.

Seam 46 should have a sufficient cross-section to urge patch 10 to a planar configuration. The outer one centimeter of mesh material of the top mesh material piece or layer 44 is left free to serve as a border or apron 51 to fill uneven voids in the patient's tissue. Free border 51 serves to frictionally keep patch 10 in the appropriate hernia repair position when the hernia mesh patch 10 is placed in a patient's preperitoneal space. Inside of the seam 46, like-size darts 59 (FIGS. 3, 4 and 6), aligned one above the other, are preferably positioned on bottom mesh layer 42 and top mesh layer 44. The presence of the darts 59 helps initially to frictionally keep the hernia mesh patch 10 in place. Thereafter, the patient's scar tissues grow in and around the darts 59 to continue to keep the hernia mesh patch in position. The outer one centimeter of top layer 44 has a cut or slit 58 that extends radially or diagonally to create scalloped or fringed edges 60 and defines tab portions 62.

The top mesh material, or bottom layer piece 42, has a cut or slit 66 transversely at the center thereof, which creates a finger access into the interior space or pouch 70 between the top and bottom layers 44, 42 of the synthetic mesh material.

In use, the surgeon uses both sharp and blunt instruments to create a pocket in a patient's preperitoneal space. The surgeon selects the type and size embodiment of the hernia mesh patch 10 best suited to be used in the repair of the patient's defect or hernia 14. The selected hernia mesh patch 10 may then be folded and further compacted by the surgeon, using his or her fingers, so that selected patch 10 may be conveniently inserted through the wound or incision 16 and down into the patient's preperitoneal space. The hernia mesh patch 10 is then released to allow the patch 10 to expand. The stiffness of seam 46 biases the patch into a planar configuration. Thereafter, the surgeon uses his or her finger to continue any further expansion of patch 10 that may be necessary. The surgeon's finger may be inserted through the slit 66 in the top mesh layer 42 to position patch 10 within the preperitoneal space. After the withdrawal of the surgeon's finger, the repair surgery is completed by closing the incision 16 with stitches.

In the repair of other hernias, and especially those at that are large, a direct incision is made. After the placement of a large hernia mesh patch, the surgeon may use limited sutures to keep the larger hernia mesh patch in place. Generally, most of the embodiments of the hernia mesh patch are positioned, and so remain, without the use of sutures.

The hernia mesh patch of the invention is simple in design and in the method of insertion. The patches adequately underlay a hernia defect by a minimum of two centimeters around the circumference of the hernia defect, with sufficient rigidity and with sufficient friction to eliminate or minimize sliding or migration. When the hernia mesh patches are used, the repair of inguinal and other abdominal wall hernias are repaired through a smaller wound or incision, with less tension, less post-operative discomfort, shorter operating time, and at a potential lower cost to the patient. The patient's post-operative discomfort is decreased, and the risk of any recurrence is likewise decreased.

While the invention has been shown in several embodiments, it should be apparent that it is not limited to those embodiments but is susceptible to various changes without departing from the scope of the invention.

What is claimed is:

1. A tissue aperture repair patch for implanting within a patient, comprising:
   two layers of inert synthetic mesh material, at least one of said layers being sized and shaped to extend across and beyond a tissue aperture in a patient;
   a seam joining said layers that imparts stiffness to the patch for biasing the patch in a planar configuration; and
   at least one of said layers of inert synthetic mesh material having a periphery extending beyond said seam that defines a border having a free outer edge to fill uneven voids in a patient's tissue.

2. The patch according to claim 1, wherein said layers of inert synthetic mesh material are ultrasonically joined to each other at said seam.

3. The patch according to claim 1, wherein said seam is arranged in one of an oval, ovoid, loop or ring configuration.

4. The patch according to claim 1, wherein said patch is configured in one of a circular, loop, ovoid, or oval shape.

5. The patch according to claim 1, wherein said layers have the same size.

6. The patch according to claim 1, wherein said seam is located approximately one centimeter inward from said free outer edge.

7. A tissue aperture repair patch for implanting in a patient, comprising:
   a first layer of inert synthetic mesh material sized and shaped to extend across and beyond a tissue aperture in a patient;
   a second layer of inert synthetic mesh material secured to the first layer by a seam to create a pouch between the first and second layers;
   an opening in the pouch for providing access to an interior of the pouch to position the patch across the tissue aperture; and
   the seam defining a periphery of said pouch between said layers, and imparting stiffness to the patch for biasing the patch into a planar configuration.

8. The patch according to claim 7, wherein:

the seam is spaced inwardly from a periphery of at least one of said first layer and said second layer, said seam defining a border between said seam and said periphery.

9. The patch according to claim 7, wherein:

said seam is in a zig-zag configuration.

10. A tissue aperture repair patch, comprising:

a first layer of inert synthetic mesh material sized and shaped to extend across and beyond hernia;

a second layer of inert synthetic mesh material overlying said first layer to create a generally planar configuration for the patch;

said first layer and said second layer being joined together by a seam that defines a periphery of a pouch between said layers, said seam imparting stiffness to the patch for biasing the patch to a planar configuration;

an opening in one of said layers for providing access to an interior of said pouch to facilitate insertion of the patch into the patient and to position the patch across the tissue aperture; and wherein the seam is spaced inwardly from a periphery of at least one of said first layer and said second layer, said seam defining a border between said seam and said periphery.

11. The patch according to claim 10, wherein:

said seam is in a zig-zag configuration.

* * * * *